United States Patent
Mankopf et al.

(10) Patent No.: US 9,661,119 B2
(45) Date of Patent: May 23, 2017

(54) METHOD AND DEVICE FOR THE WIRELESS CONTROL OF A MEDICAL DEVICE

(71) Applicant: MAQUET GMBH, Rastatt (DE)

(72) Inventors: Michael Mankopf, Möhrendorf (DE); Michael Fruh, Achern (DE); Jürgen Ruch, Offenburg (DE)

(73) Assignee: MAQUET GMBH, Rastatt (DE)

( * ) Notice: Subject to any disclaimer, the term of this patent is extended or adjusted under 35 U.S.C. 154(b) by 0 days.

(21) Appl. No.: 14/761,023

(22) PCT Filed: Jan. 16, 2014

(86) PCT No.: PCT/EP2014/050801
§ 371 (c)(1),
(2) Date: Jul. 15, 2015

(87) PCT Pub. No.: WO2014/111468
PCT Pub. Date: Jul. 24, 2014

(65) Prior Publication Data
US 2016/0028874 A1    Jan. 28, 2016

(30) Foreign Application Priority Data
Jan. 16, 2013 (DE) .................. 10 2013 100 428

(51) Int. Cl.
*H04M 1/725* (2006.01)
*H04W 4/00* (2009.01)
*G06F 19/00* (2011.01)

(52) U.S. Cl.
CPC .... *H04M 1/72533* (2013.01); *G06F 19/3406* (2013.01); *H04W 4/008* (2013.01); *G06F 19/3418* (2013.01)

(58) Field of Classification Search
CPC . H04B 5/0062; H04B 1/38; H04L 2012/2841;
H04L 67/125; H04W 4/008;
(Continued)

(56) References Cited

U.S. PATENT DOCUMENTS

| 2003/0093503 A1 | 5/2003 | Yamaki et al. |
| 2006/0012488 A1* | 1/2006 | Hilbrink ............... G08C 17/00 340/12.22 |

(Continued)

FOREIGN PATENT DOCUMENTS

| CN | 101465044 A | 6/2009 |
| CN | 101808571 A | 8/2010 |

(Continued)

OTHER PUBLICATIONS

International Search Report for PCT Serial No. PCT/EP2014/050801 dated May 26, 2014.

(Continued)

*Primary Examiner* — Nizar Sivji (57) ABSTRACT

A device and a method for the wireless control of a medical device (30) by means of a remote control (10, 60, 70, 80), in which via at least one first input unit (12) provided via a touchscreen of the remote control (10, 60, 70, 80) at least one control information for activating and/or deactivating a control function for controlling the device (30) is input. At least one release information is input via a second input unit (18, 84) of the remote control (10, 60, 70, 80) which is independent of the first input unit (12). When the control information is input, the control function is only activated and/or deactivated when the release information is input via the second input unit.

20 Claims, 5 Drawing Sheets

(58) Field of Classification Search
CPC .......... H04W 52/028; F24F 11/001; F24F 2011/0091; G05B 2219/23051; G05B 2219/23178; G05B 2219/23297; G05B 2219/2633; G08C 17/02; G08C 2201/93; G08C 2201/32; G08C 2201/70; G08C 2201/51; G08C 25/02; G08C 2201/40; G08C 2201/42; G08C 2201/50; H04N 2005/4432; H04N 5/4403; H04N 2005/4444; H04N 21/4131; H04N 21/42208; H04N 21/42224; H04N 21/42225; H04N 21/4312; H04N 21/4415; H04N 5/44513; H04N 7/12; H04M 1/72533; H04M 1/7253; H04M 2250/02

See application file for complete search history.

(56) References Cited

U.S. PATENT DOCUMENTS

| | | |
|---|---|---|
| 2008/0125064 A1 | 5/2008 | Das et al. |
| 2009/0080348 A1 | 3/2009 | Hamel et al. |
| 2011/0055447 A1 | 3/2011 | Costa |
| 2012/0112890 A1 | 5/2012 | Rawls-Meehan |
| 2013/0247117 A1* | 9/2013 | Yamada .......... G08C 17/02 725/93 |

FOREIGN PATENT DOCUMENTS

| | | |
|---|---|---|
| CN | 102047256 A | 5/2011 |
| DE | 10 2005 054 223 A1 | 5/2007 |
| DE | 10 2005 054 230 A1 | 5/2007 |
| DE | 10 2007 060 808 A1 | 3/2009 |
| DE | 10 2007 060 811 A1 | 3/2009 |
| DE | 10 2007 060 810 A1 | 6/2009 |
| GB | 2475091 | 5/2011 |
| JP | 2009-177796 A | 8/2009 |
| JP | 2011-072370 A | 4/2011 |
| JP | 2011-161113 A | 8/2011 |
| JP | 2011-523869 A | 8/2011 |
| WO | 2006052801 A1 | 5/2006 |

OTHER PUBLICATIONS

Chinese Office Action (English and Chinese translations) issued Dec. 19, 2016 for corresponding Chinese Patent Application No. 201480004730.7, 19 pages.

* cited by examiner

METHOD AND DEVICE FOR THE WIRELESS CONTROL OF A MEDICAL DEVICE

CROSS REFERENCE TO RELATED APPLICATIONS

This application is entitled to the benefit of and incorporates by reference subject matter disclosed in International Patent Application No. PCT/EP2014/050801 filed on Jan. 16, 2014, and German Application No. 10 2013 100 428.8 filed on Jan. 16, 2013.

TECHNICAL FIELD

The invention relates to a method and a device for the wireless control of a medical device by means of a remote control.

BACKGROUND

For operating medical devices, such as operating tables, a plurality of solutions as disclosed, for example, in documents DE 10 2005 054 230 A1, DE 10 2007 060 810 A1, DE 10 2007 060 808 A1, DE 10 2007 060 811 A1 and DE 10 2005 054 223 A1, are known. Further, from the field of consumer electronics a plurality of programmable and teachable remote controls are known which, however, do not meet the high demands on remote controls for medical devices with respect to fail-safeness.

SUMMARY

Starting out from the known prior art, the object of the invention is to specify a method and an arrangement for the wireless control of a medical device by means of a remote control by which a comfortable and safe operation of the medical device is possible.

This object is solved by a method for the wireless control of a medical device by means of a remote control, in which via at least one first input unit provided by a touchscreen of the remote control at least one control information for activating and/or deactivating a control function for controlling the device is input, via a second input unit of the remote control which is independent of the first input unit at least a release information is input, and in which, when the control information is input, the control information is only activated and/or deactivated when the release information is input via the second input unit as well as by an arrangement comprising a housing for receiving a separately usable device which has at least one input unit, provided via a touchscreen, in the form of a separate usable device for the input of at least one control information for activating and/or deactivating a control information for controlling the medial device to be controlled, wherein the housing includes a second input unit for the input of at least one release information, which second input unit is independent of the first input unit.

By the invention, a simple electrical device having a touchscreen and being coupled to a further input unit can be used as a remote control for controlling a medical device. Such a simple electrical device can be a smartphone, a media player or a tablet computer, in particular an iPod, an iPhone or an iPad of the company Apple Computer Incorporation.

According to the invention, the control function is only performed when a control information has been input by means of the first input unit and a release information has been input via the second input unit that is independent of the first input unit. As a result, inadvertent inputs via the first input unit do not directly result in the control function so that the inadvertent control of the medical device is prevented. In particular, in the case of an inadvertent operation of a medical device used in the treatment of a patient or during the surgical operation of a patient, an inadvertent operation would have fatal consequences for the health and the life of the patient. At least the first and the second input unit are part of the remote control for the wireless control of the medical device.

In an advantageous development, the control information is only sent from the remote control to the device when the control information is input via the first input unit and the release information is input via the second input unit at the same time or within a preset time window. In this way, it is achieved that there must be a close temporal connection between the input of the control information and the input of the release information so that operating errors are effectively prevented.

Further, it is advantageous when data with the control information are transmitted from a first control unit of the first input unit to a second control unit of the second input unit, and when the control information is only transmitted from the second control unit further to the medical device to be controlled when the release information is detected by the control unit simultaneously or within a preset time window. By providing the second control unit, it can easily be monitored whether the release information is present at the same time or within a preset time window after transmission of the control information from the first control unit to the second control unit. As a result, the inventive dependence of the sending of the control information on the presence of the release information can easily be realized without structural changes to the first input unit or to the medical device to be controlled being necessary. In particular, this is particularly advantageous when as a first input unit a simple electrical device having a touchscreen is used. As a result, an easy cost-efficient realization of a remote control for the wireless control of a medical device is possible. Preferably, the simple electrical device serves in combination with the second input unit as a remote control. The simple electrical device is preferably at least in part received in a housing in which also the second input unit is received, wherein the arrangement of the simple electrical device, the second input unit and the housing form the remote control for the wireless control of the medical device. The time window preferably comprises a range of 2 seconds before the input of the control information up to 2 seconds after the input of the control information, preferably 1 second before the input of the control information to 1 second after the input of the control information, in particular 0.5 seconds before the input of the control information up to 0.5 seconds after the input of the control information.

Alternatively or additionally, the control function of the medical device is only activated and/or deactivated by a control unit of the device when the control information and the release information are transmitted from the remote control to the device within a preset time window or at the same time. In this way, alternatively or additionally, the presence of the release information can be checked in the medical device to be controlled itself. As a result, a high degree of safety is achieved. The time window preferably comprises a range of 2 seconds before the input of the control information up to 2 seconds after the input of the control information, preferably 1 second before the input of the control information to 1 second after the input of the control information, in particular 0.5 seconds before the input of the control information up to 0.5 seconds after the input of the control information.

Further, it is advantageous when the second input unit is provided by at least one switching transponder which comprises a transponder and an actuating element connected thereto. The actuating element can, for example, be a push button. As a transponder, an active transponder or a passive transponder can be used. Active transponders have an own energy supply. This energy supply can be realized by a battery arranged in the remote control or an accumulator arranged therein. Alternatively or additionally, the energy supply of the active transponder can also be supplied with energy by a battery or an accumulator of the first input unit. Active transponders generally have a higher reach than passive transponders. Passive transponders obtain the energy required for the communication and for the execution of internal processes exclusively from the field of a write/read unit so that the passive transponders do not require an own power supply, the communication reach of passive transponders generally being less than the one of active transponders. However, in the prior art possibilities are known to also increase the reach of passive transponders. A device and a method for the wireless energy and/or data transmission between a source device and at least one target device are, for example, known from document DE 10 2007 060 811 A1, the content of which is herewith incorporated by reference into the present specification.

Further, it is advantageous when the switching transponder communicates at least in one switching state of the actuating element with a communication unit, preferably with a read unit, wherein the communication unit is connected to the control unit of the device at least via one data line. As a result, an easy communication of the switching transponder with the control unit of the medical device via the communication unit is possible. The data line between the communication unit and the medical device can be designed as a wire-bound data line or as a wireless data line. Further, the communication unit can be integrated into the medical device to be controlled.

It is particularly advantageous when the transponder is a passive, half-active or active RFID tag. In this way, an easy and cost-efficient communication between the second input unit and the medical device to be controlled and/or the first input unit can take place.

Further, it is advantageous when the energy supply of the transponder at least with the energy required for the communication with a communication unit is provided via a wireless coupling to an energy supply unit each time, wherein the energy supply unit is preferably a part of the communication unit. As a result, the transponder can obtain the energy required for its operation easily from the field of a communication unit designed as a write/read unit.

Further, it is advantageous when the wireless communication between the transponder and a communication unit takes place in the UHF transmission band. Thus, an easy and safe data transmission is possible.

Further, it is advantageous when the actuating element of the second input unit short-circuits the receiving circuit of the transponder in a first switch position of the actuating element, wherein the energy supply unit electrically and/or electro-magnetically transmits the energy required by the transponder at least for the communication with at least one communication unit to the receiving circuit. In a second switch position of the actuating element, the transponder can transmit an information to the communication unit, in particular an ID of the transponder, which is evaluated by the communication unit and is interpreted as a release information.

It is particularly advantageous when the second input unit does not comprise an exchangeable battery nor a chargeable accumulator. This can, in particular, be achieved in that the power supply of the second input unit takes place via the power supply of the first input unit, or the electrical energy required for its operation is derived from an electric or electromagnetic field provided by a communication unit designed as a write/read unit.

It is particularly advantageous when the second input unit has a housing with a receiving compartment in which the first input unit is received such that the touchscreen of the first input unit is operable. As a result, a simple structural unit composed of the first input unit and of the second input unit can be realized which can be handled easily as a general arrangement by one operator. It is particularly advantageous when the first input unit is inserted into the receiving compartment. In this way, the first input unit can be held in the housing easily and safely. Further, it is then also easily possible to establish an electric plug connection between the housing and the first input unit.

Via such a plug connector, a power supply of the first input unit can be provided and/or data can be transmitted between a control unit of the first input unit and a second control unit arranged in a housing. Alternatively or additionally, via the plug connector also a power supply of the second input unit or of the second control unit arranged in the housing can be provided. As a result, a particularly easy power supply and/or coupling of the first input unit and the second input unit is possible.

It is particularly advantageous when the release information is input via an actuating element of the second input unit, preferably via a push button, which is arranged outside the receiving area and is accessible from the outside of the housing. As a result, an easy operation is possible, wherein such a push button and/or the pressing motion that can be performed by means of the push button can easily be perceived, preferably haptically, by an operator.

It is particularly advantageous when a drive of the medical device to be controlled in particular an actuator and/or a drive for a locking element is activated and/or deactivated by means of the control function. As a result, a plurality of control functions of the medical device can easily be provided by means of the remote control.

It is particularly advantageous when the medical device is an operating table. Then, an operating function can easily be performed in particular during the surgical operation of the patient by means of the remote control.

It is particularly advantageous when the data with the control information and/or the release information are transmitted from the first input unit, from the second input unit and/or from the second control unit to the medical device to be controlled in an encrypted manner. In particular, these data can be transmitted in a repeatedly symmetrically encrypted manner. As a result, manipulations and inadvertent operating errors can be prevented since both data having a different cryptographic encoding cannot be processed by the control unit of the medical device so that inadvertent operating errors are prevented and malicious manipulations which harm the user and/or the patient are effectively prevented.

The device claimed according to a second aspect of the invention for the wireless control of a medical device can in particular be further developed in that the first input unit has a keyboard for the input of control information provided via the touchscreen and that the second input unit has an actuating element for the input of the release information. As a result, an easy and comfortable input of the control information and of the release information is possible.

Further, it is advantageous to arrange at least one control unit in the housing, which control unit causes that the control information is sent to the device when the release information is present at the same time or within a preset time window before and/or after the input of control information. As a result, the fail-safeness can be increased and faulty inputs can be prevented. The time window preferably comprises a range of 2 seconds before the input of the control information up to 2 seconds after the input of the control information, preferably 1 second before the input of the control information up to 1 second after the input of the control information, in particular 0.5 seconds before the input of the control information up to 0.5 seconds after the input of the control information.

Further, it is advantageous to arrange a control unit, preferably a transponder, within or on the housing. When the actuating element of the second input unit is actuated, the control unit or the transponder sends a release signal to the device to be operated or stops the sending of a blocking signal to the medical device to be operated. The control information is then transmitted to the device to be operated independent of the presence of the release information. A control unit of the device checks whether at the same time or within the time window, i.e. shortly before or shortly after the receipt of the control information, the release signal has been sent. As a result, operating errors can be prevented easily and effectively.

BRIEF DESCRIPTION OF THE DRAWINGS

Further features and advantages of the invention result from the following description which explains the invention in more detail on the basis of embodiments in connection with the enclosed Figures.

DETAILED DESCRIPTION

Figure 1:
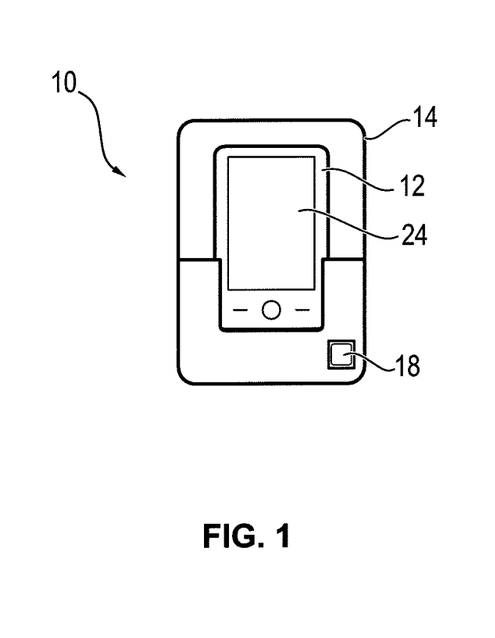
FIG. 1 shows a remote control for the wireless control of a medical device according to a first embodiment of the invention, which remote control comprises a smartphone and a docking station.

FIG. 1 shows a remote control 10 comprising a smartphone 12 and a docking station 14. The smartphone 12 serves as a first input unit of the remote control 10. The first input unit 12 comprises a touchscreen 24 for the input of a control information for activating and/or deactivating a control function of a medical device to be controlled, in the present embodiment for controlling an operating table 30 illustrated in FIG. 3. The docking station 14 comprises a second input unit for the input of a release information, which second input unit is formed as a push button 18. In the first embodiment of the invention, the transmission of the control information input via the first input unit takes place via the docking station 14 to the medical device 30 to be controlled. However, the docking station 14 only transmits the control information to the medical device 30 to be controlled when the release information is input via the push button 18 simultaneously to the input of the control information via the first input unit 12, i.e. the push button 18 has to be pressed when the control information is input via the first input unit.

Alternatively or additionally, the control information can also be transmitted from the docking station to the medical device to be controlled when the release information is provided shortly before or shortly after the input of the control information via the first input unit. Here a period of time of give or take two seconds, preferably give or take one second or give or take 0.5 seconds is regarded as a time period for the close temporal connection of the input of the release information before or after the input of the control information. In this way, it is guaranteed that the input of the control information and the input of the release information have to be in close temporal connection so that the control function of the device 30 is performed.

Figure 2:
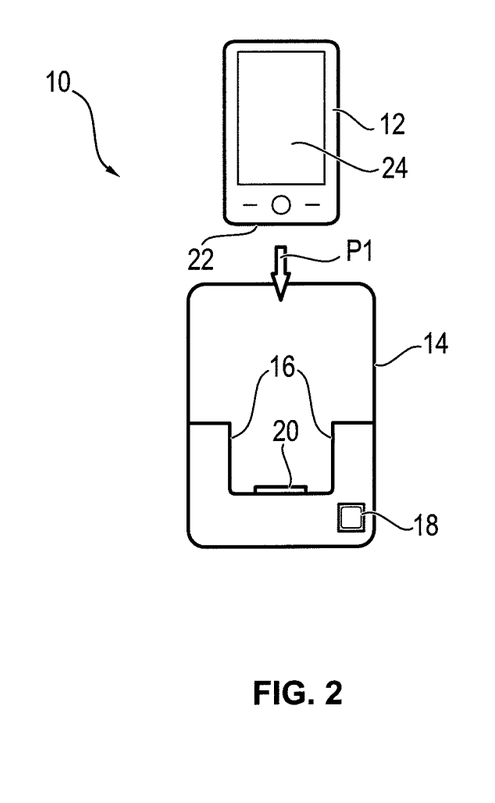
FIG. 2 shows the smartphone and the docking station according to FIG. 1 in the separated state.

The docking station 14 and the smartphone 12 together form the remote control 10. In FIG. 2, the smartphone 12 and the docking station 14 are shown in the separated state. For connecting the smartphone to the docking station 14, the smartphone is inserted in the direction of the arrow P1 into lateral receiving areas 16 of the docking station 14 until a plug connector 20 of the docking station 14 is connected to a complementary plug connector 22 of the smartphone 12. For the input of the at least one control function, the smartphone has a touchscreen 24 via which at least one input field for the input of the control information is provided. Alternatively or additionally, the touchscreen can provide a text input field via which a control command for generating the control information can be input. Further, display fields for the display of status information received by the remote control 10 can be provided.

Figure 3:
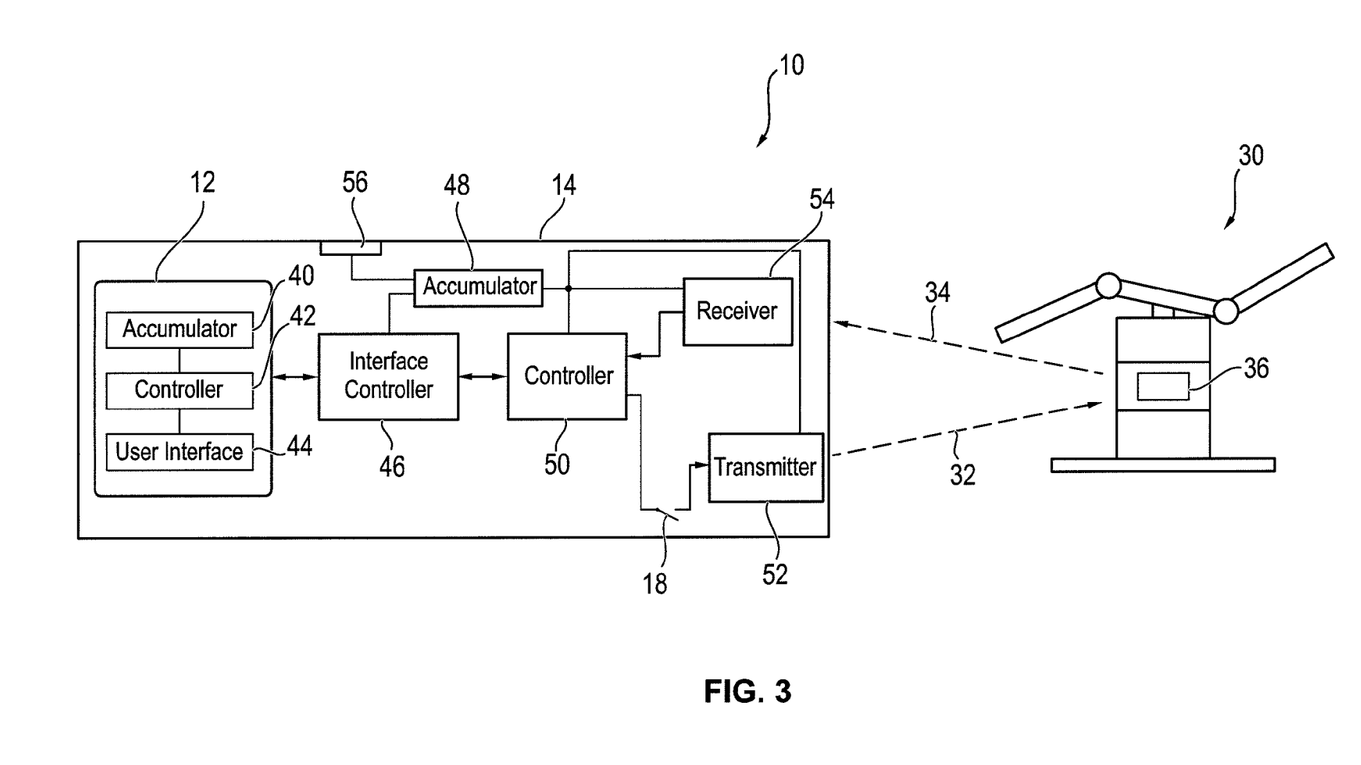
FIG. 3 shows a block diagram of the remote control according to FIGS. 1 and 2 for the wireless control of an operating table.

In FIG. 3, a block diagram of the remote control 10 is illustrated together with a schematic illustration of the operating table 30 to be operated. The smartphone 12 includes an accumulator 40 for power supply, a controller 42 and a user interface 44 designed as a touchscreen 24. The smartphone 12 is connected to an interface controller 46 of the docking station 14 via the plug connectors 20, 22. The docking station 14 further has an accumulator 48, a docking station controller 50, a transmitter unit 52 for transmitting control information 32 to a communication unit 36 of the operating table and a receiver unit 54 for receiving status information and/or confirmation requests of the communication unit 36 of the operating table 30. The docking station 14 has a further plug connector 56 via which at least electrical energy for charging the accumulator 48 can be supplied to the docking station 14. The accumulator 40 of the smartphone 12 can be charged by a power supply provided by the interface controller 46 and supplied from the accumulator 48 or, alternatively, directly by a power supply via the plug connector 56. The interface controller 46 in particular transmits the control information input via the touchscreen of the smartphone 12 to the docking station controller 50 and transmits the status information 34 of the operating table 30 which is sent by the operating table 30, received by the receiving unit 54 and processed by the docking station controller 50 to the smartphone 12 which outputs the status information via the touchscreen 24 and/or outputs a selection of control functions dependent on the status information via the touchscreen 24. The transmission of the control information to be sent from the controller 50 to the transmitter 52 only takes place when the push button 18 is closed.

In alternative embodiments, the push button 18 can be connected to an input of the docking station controller 50 so that it detects the pressing states of the push button 18 and, dependent on the pressing states, transmits at least a part of the control information input via the touchscreen 24 only to the transmitting unit 52 when the actuation of the push button 18 has been detected by the docking station controller 50. Preferably, in special embodiments only such control information is transmitted dependent on the switching state 18 from the docking station controller 50 to the transmitting unit 52 which could directly result in a negative effect on the treatment of the patient when activated inadvertently.

Figure 4:
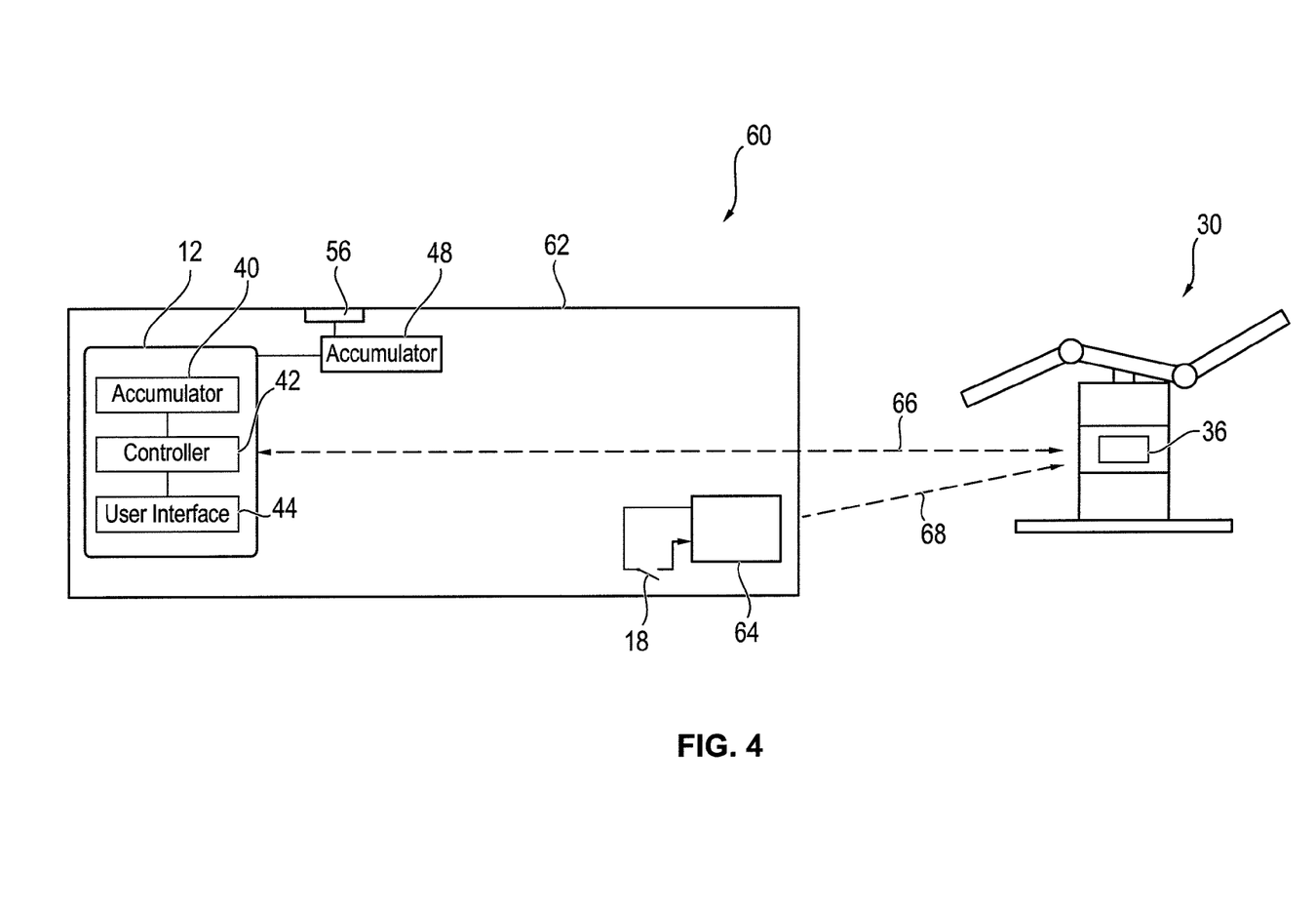
FIG. 4 shows a block diagram of a remote control for the wireless control of an operating table according to a second embodiment of the invention, which remote control comprises a smartphone and a docking station.

In FIG. 4, a block diagram of a remote control 60 with a docking station 62 and the smartphone 12 according to a second embodiment is shown. Elements having the same structure or the same function are identified with the same reference signs. Like the docking station 14 according to FIG. 3, the docking station 62 has an accumulator 48 which serves as an additional power supply for the smartphone 12 and to charge the accumulator 40 of the smartphone 12. The accumulator 48 is connectable via the plug connector 56 to an external power supply unit (not illustrated) and can easily be charged via this plug connection 56. In contrast to the remote control 10 according to the first embodiment, the smartphone 12 sends a control information 66 to the communication unit 36 of the operating table 30 to be controlled independent of the actuating state of the push button 18. The data transmission between the communication unit 36 and the smartphone 12 is bi-directional, i.e. status information of the operating table 30 are likewise transmitted from the communication unit 36 to the smartphone 12.

The docking station 62 further has a passive transmitting unit 64, which, when supplied with power by the communication unit 36 of the operating table 30 designed as a write/read unit, transmits an information to the communication unit 36 of the operating table 30 dependent on the switching state of the push button 18, which information is interpreted as a release information by the communication unit 36. The communication unit 36 and/or a further control unit of the operating table 30 only executes the control function when at the same time the input information of the release information has been received and/or when the receipt of the control information and of the release information are in close temporal connection. What is regarded as close temporal connection here has already been explained in connection with the first embodiment of the invention. The passive transmitting unit is a passive transponder in the present embodiment. In other embodiments, also other, in particular active transmitting units can be employed.

Figure 5:
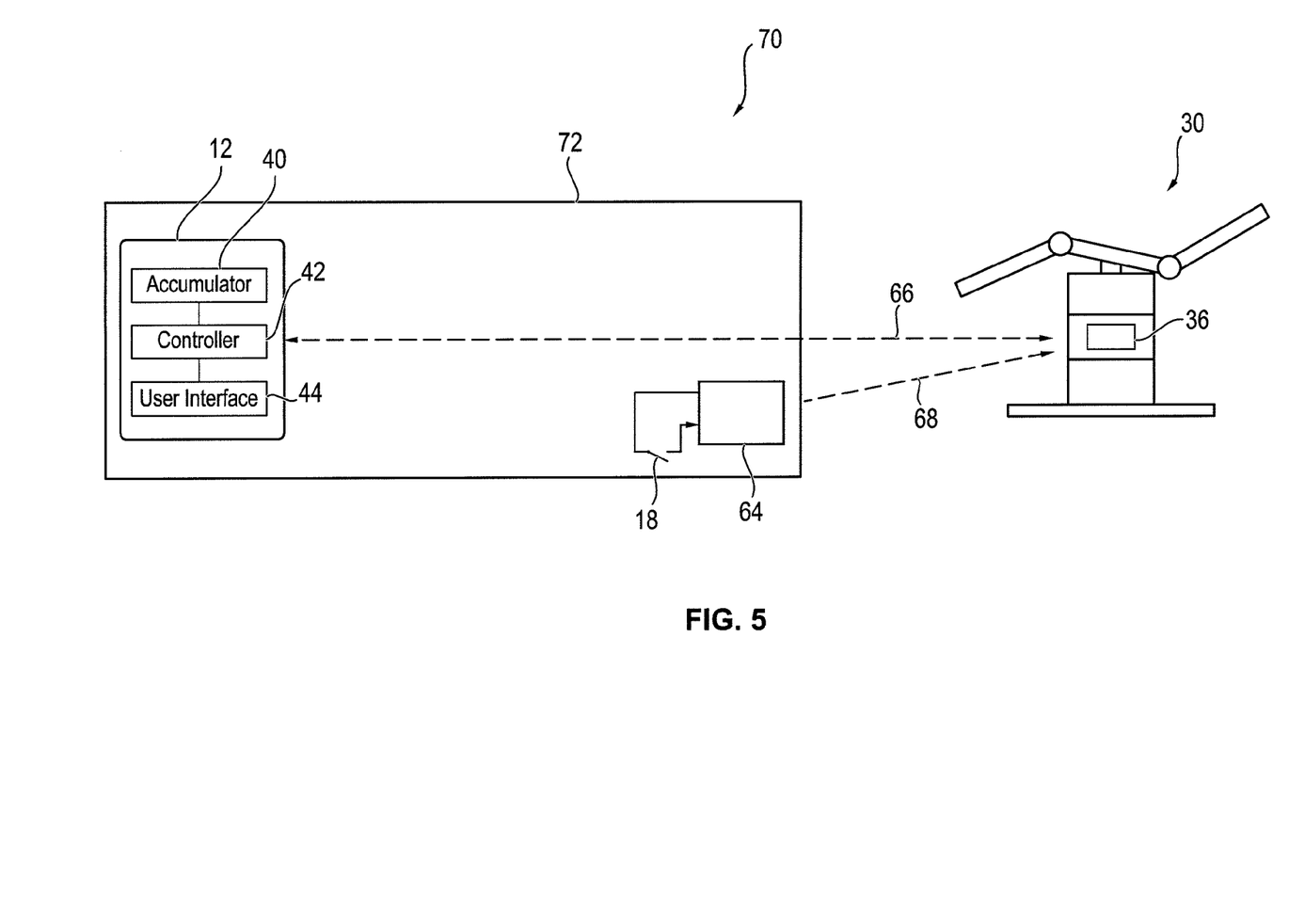
FIG. 5 shows a block diagram of a remote control for the control of an operating table according to a third embodiment of the invention, which remote control comprises a smartphone and docking station.

In FIG. 5, a block diagram of a remote control 70 having a docking station 72 and the smartphone 12 is shown according to a third embodiment. In contrast to the remote control 60 according to the second embodiment, the docking station 72 of the remote control 70 of the third embodiment has no accumulator. The function of the transmitter 64 for generating and transmitting the release information 68 and the generation of the control information 66 by means of the smartphone 12 and the transmission of the control information to the communication unit 36 of the operating table 30 takes place in the same manner as explained in connection with the second embodiment of the invention. The plug connector 20 of the docking station 72 is connected to a further plug connector 74 of the docking station 72 so that at least the power supply and preferably also the data exchange between an external control unit and the smartphone 12 is possible via the plug connectors 74, 20, 22.

The data transmission between the smartphone 12 and the communication unit 36 can take place in a wireless manner in all three described embodiments. In particular, the data transmission takes place from the smartphone 12 to the communication unit 36 of the operating table 30 via one of the communication types WIFI, Bluetooth, infrared, near field communication and/or radio signals. Here, the transmission of the control information from the smartphone 12 to the communication unit 36 can take place according to a first communication type and the transmission of information from the communication unit 36 to the smartphone 12 according to another communication type.

Figure 6:
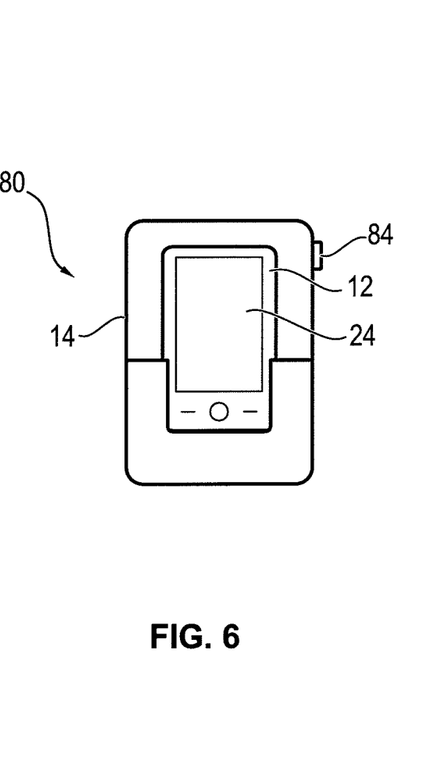
FIG. 6 shows a remote control according to a fourth embodiment of the invention, which remote control comprises a smartphone and a docking station.
Figure 7:
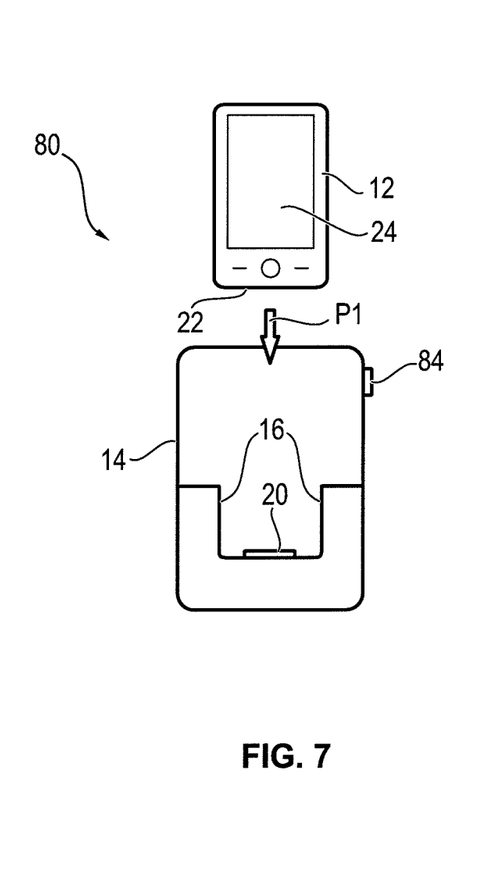
FIG. 7 shows the smartphone and the docking station according to FIG. 6 in a separated state.

FIGS. 6 and 7 show a remote control 80 comprising a docking station 82 and a smartphone 12 according to a fourth embodiment of the invention. In contrast to the remote control 10 of the first embodiment of the invention, the docking station 82 has a push button 84 on its right exterior side in the upper third which serves as a second input unit. By means of this remote control 80, the control sequences described in FIGS. 3 to 5 and described in connection with the first, second and third embodiment are alternative options.

As a docking station, a housing having a second input unit is regarded which is mechanically couplable to the electrical device serving as a first input unit and having a touchscreen. It is particularly advantageous when the device received in the docking station is completely enclosed by the docking station at at least four, preferably at five sides. It is particularly advantageous when the housing of the docking station also covers the sixth side of the electrical device having the touchscreen, wherein display readings on the touchscreen are still visible through the covers and the touchscreen is operable through the cover.

The docking station is preferably formed as a cover, i.e. an enclosure, into which the smartphone 12 is inserted. The further elements shown in the block diagrams of FIGS. 3 to 5 are integrated into the cover as electronic circuits. The smartphone 12 is received in this cover. The electronic circuit has an interface to the smartphone 12 which can be wire-bound or wireless.

As a wire-bound interface, a USB interface can be used, preferably via a micro USB connector. As a wireless interface, a Bluetooth connection can be employed. The transmitting unit 52 and the receiving unit 54 which are provided for communication with the medical device 30 to be controlled are based on an infrared transmission and/or a radio transmission. The data transmission between the controller 50 of the docking station 14 and the smartphone 12 is preferably bi-directional so that also status messages of the medical device can be transmitted to the smartphone 12 for display and/or for further processing.

Alternatively to the smartphone 12 described in FIGS. 1 to 7, also other electrical devices having a touchscreen can be employed, such as media players, tablet computers, in particular an iPad or an iPod of the company Apple Computers Incorporation.

Although various embodiments of the present invention have been described and shown, the invention is not restricted thereto, but may also be embodied in other ways within the scope of the subject-matter defined in the following claims.

What is claimed is:

1. A method for the wireless control of a medical device by a remote control, comprising:
   via a first input unit provided by a touchscreen of the remote control a control information for activating or deactivating a control function for controlling the medical device being input,
   via a second input unit of the remote control which is independent of the first input unit at least a release information being input,
   and in which, when the control information is input via the first input unit, the control information is only activated or deactivated when the release information is input via the second input unit,
   wherein the control information is only sent from the remote control to the medical device when the control information is input via the first input unit and the release information is input via the second input unit at the same time or within a preset time window,
   wherein the release information is input via the second input unit being pressed;
   wherein the control information is transmitted in an encrypted manner from the first input unit to the medical device,
   wherein the release information is transmitted in an encrypted manner from the second input unit to the medical device, and
   wherein the medical device only executes the control function when the encrypted control information and the encrypted release information are received by a control unit of the medical device at the same time or within a preset time window.

2. The method according to claim 1, wherein data with the control information are transmitted from the first control unit of the first input unit to a second control unit of the second input unit, and
   the control information is only transmitted from the second control unit further to the medical device when the release information is determined simultaneously or within the preset time window by the second control unit.

3. The method according to claim 1, wherein the control function of the medical device is only activated or deactivated by the control unit of the medical device when a first cryptographic encoding of the control information is not different from a second cryptographic encoding of the release information.

4. The method according to claim 1, wherein the first input unit is provided by a smartphone, a tablet computer or a portable digital media player.

5. The method according to claim 1, wherein the second input unit is provided by a switching transponder which comprises a transponder and an actuating element connected thereto.

6. The method according to claim 5, wherein the switching transponder communicates at least in one switching state of the actuating element with a communication unit that is a read unit, the communication unit being connected to a control unit of the medical device at least via one data line.

7. The method according to claim 1, wherein the second input unit has a housing with a receiving compartment in which the first input unit is received such that the touchscreen of the first input unit is operable.

8. The method according to claim 7, wherein:
   the first input unit is inserted into the receiving compartment; and
   the housing is a docking station.

9. The method according to claim 7, wherein the first input unit is connected via a plug connector to the housing,
   wherein via the plug connector a power supply of the first input unit is provided or data are transmitted between a control unit of the first input unit and a second control unit arranged in the housing.

10. The method according to claim 7, wherein:
    the release information is input via an actuating element of the second input unit that is accessible from the outside of the housing and arranged outside the receiving area; and
    the second input unit is a push button.

11. The method according to claim 1, wherein by the control function a drive of the medical device to be controlled is activated or deactivated, in particular an actuator or a drive for a locking element.

12. The method according to claim 1, wherein the medical device to be controlled is an operating table.

13. The method according to claim 1, wherein data with the control information or with the release information are transmitted in a repeatedly symmetrically encrypted manner from the first input unit, from the second input unit or from the second control unit to the medical device.

14. A device for the wireless control of a medical device, comprising
    a housing for receiving a separately usable device which has a first input unit, provided via a touchscreen, in the form of a separate usable device for the input of a control information for activating or deactivating a control information for controlling the medical device to be controlled,
    wherein the housing includes a second input unit for the input of a release information, the second input unit being independent of the first input unit,
    wherein the housing is a docking station,
    wherein the control information is transmitted in an encrypted manner from the first input unit to the medical device,
    wherein the release information is transmitted in an encrypted manner from the second input unit to the medical device, and
    wherein the medical device only executes a control function when the encrypted control information and the encrypted release information are received by a control unit of the medical device at the same time or within a preset time window.

15. The device according to claim 14, wherein data with the control information are transmitted from a first control unit of the first input unit to a second control unit of the second input unit,
    the control information is only transmitted from the second control unit further to the medical device when the release information is determined simultaneously or within a preset time window by the second control unit, and
    the release information is input via the second input unit being pressed.

16. The method according to claim 1, wherein the first input unit is provided by a smartphone.

17. The device according to claim 14, wherein the first input unit is provided by a smartphone.

18. The method according to claim 1, wherein the second input unit is provided by a switching transponder which comprises a transponder and an actuating element connected thereto.

19. The device according to claim 14, wherein the second input unit is a push button.

20. A device for the wireless control of an operating table, comprising
- a housing for receiving a separately usable device which has a first input unit, provided via a touchscreen, in the form of a separate usable device for the input of a control information for activating or deactivating a control function for controlling the operating table to be controlled,
- wherein the housing includes a second input unit for the input of a release information, the second input unit being independent of the first input unit,
- wherein the housing is a docking station,
- wherein the first input unit is provided by a smartphone,
- wherein the control information is transmitted from the first input unit to the operating table in an encrypted manner,
- wherein the release information is transmitted from the second input unit to the operating table in an encrypted manner, and
- wherein the operating table only executes the control function when the encrypted control information and the encrypted release information are received by a control unit of the operating table at the same time or within a preset time window.

* * * * *